United States Patent
Brosch et al.

(10) Patent No.: US 6,500,994 B1
(45) Date of Patent: Dec. 31, 2002

(54) PURIFICATION OF 1,1,1,3,3-PENTAFLUOROBUTANE

(75) Inventors: Carsten Brosch, Hannover (DE); Heinz Gress, Hannover (DE); Matthias Rieland, Hannover (DE)

(73) Assignee: Solvay Fluor und Derivate GmbH, Hannover (DE)

( * ) Notice: Subject to any disclaimer, the term of this patent is extended or adjusted under 35 U.S.C. 154(b) by 0 days.

(21) Appl. No.: 09/786,589

(22) PCT Filed: Aug. 24, 1999

(86) PCT No.: PCT/DE99/02710

§ 371 (c)(1),
(2), (4) Date: Jun. 8, 2001

(87) PCT Pub. No.: WO00/14040

PCT Pub. Date: Mar. 16, 2000

(30) Foreign Application Priority Data

Sep. 3, 1998 (DE) .......................... 198 40 099

(51) Int. Cl.[7] .......................... C07C 19/08; C07C 17/38
(52) U.S. Cl. ..................... 570/134; 570/177; 570/178; 570/179; 570/180
(58) Field of Search ........................ 570/177, 178, 570/179, 180, 134

(56) References Cited

U.S. PATENT DOCUMENTS

| 3,696,156 A | * | 10/1972 | Weeks |
| 5,001,287 A | * | 3/1991 | Fernandez et al. |
| 5,300,714 A | * | 4/1994 | Pothapragada et al. |
| 5,569,797 A | | 10/1996 | Fu et al. |
| 5,621,152 A | | 4/1997 | Jansen et al. |
| 5,892,137 A | | 4/1999 | Bertocchio |

FOREIGN PATENT DOCUMENTS

| DE | 2310749 | 9/1974 |
| DE | 3311751 | 10/1994 |
| EP | 0 370 688 | 11/1989 |
| EP | 0 905 085 | 3/1999 |
| WO | 90/08750 | 8/1990 |
| WO | 97/37955 | 10/1997 |
| WO | 00/14040 | 3/2000 |

* cited by examiner

Primary Examiner—Alan Siegel
(74) Attorney, Agent, or Firm—Crowell & Moring LLP

(57) ABSTRACT

A process for purification of 1,1,1,3,3-pentafluorobutane (HFC-365mfc) containing a decreased amount of hydrogen chloride, hydrogen fluoride and/or unsaturated impurities. To this end crude 1,1,1,3,3-pentafluorobutane is treated in the liquid phase with a solid, inorganic sorption agent and/or with diatomic molecules which and to C—C multiple bonds. The product to be purified is preferably treated with elemental fluorine. The contents of hydrogen chloride and hydrogen can each be decreased to below 1 ppm. The content of unsaturated (chlorine)-fluorine-compounds can be decreased to below 20 ppm, and the content of unsaturated C2 compounds can be decreased to below 10 ppm. It has also been discovered that fluorotrichloroethylene can be used as a control substance to monitor the purification of 1,1,1,3,3-pentafluorobutane.

12 Claims, No Drawings

PURIFICATION OF 1,1,1,3,3-PENTAFLUOROBUTANE

This application is a 371 of PCT/DE99/02710 filed Aug. 24, 1999.

The invention relates to a process for producing purified 1,1,1,3,3-pentafluorobutane (HFC-365mfc).

1,1,1,3,3-pentafluorobutane is used, for example, as a propellant in the production of foamed synthetic resins. It may be produced, for example, from the corresponding pentachlorobutane compound, hydrogen fluoride and a fluorination catalyst. 1,1,1,3,3-pentafluorobutane produced in this way can contain hydrogen chloride, hydrogen fluoride or unsaturated carbon compounds that derive from the fluorination reaction or the starting material. It is desirable to produce a purified product from this impure product. This object is achieved by the process according to the present invention.

The process according to the invention provides that purified 1,1,1,3,3-pentafluorobutane with a decreased content of HCl, HF and/or unsaturated impurities is produced from crude 1,1,1,3,3-pentafluorobutane by treating the crude 1,1,1,3,3-pentafluorobuatane in the liquid phase with a solid inorganic sorption agent or diatomic molecules which add to C—C-multiple bonds and by separating the treated 1,1,1,3,3-pentafluorobutane.

Pressure and temperature are selected such that the process is carried out in the liquid phase. Preferably, the pressure is from 1 to 5 atm (abs).

Solid inorganic sorption agents can be used to separate both the acid components and also the unsaturated impurities. Diatomic molecules allow the derivatization of the unsaturated compounds to non-toxic compounds and/or compounds that can be separated by distillation.

Preferred solid inorganic sorption agents are activated carbon and sorbents composed of aluminum oxide or silicon dioxide. They are particularly well suited for separating hydrogen chloride and/or hydrogen fluoride.

The treatment with the sorption agent is advantageously carried out at a temperature from −30° C. to +100° C., preferably 15° C. to 25° C.

To decrease the content of unsaturated compounds, hydrogen chloride or elemental fluorine, chlorine or hydrogen is used as the preferred diatomic molecule.

One possible procedure is initially to decrease the content of unsaturated compounds by means of said diatomic molecules and subsequently to decrease further impurities by means of a solid inorganic sorption agent.

To decrease the content of unsaturated compounds, it is particularly preferred to use elemental fluorine, preferably in a mixture with an inert gas, such as nitrogen or argon. The treatment with elemental fluorine (or its mixtures with inert gas) is advantageously carried out at a temperature in the range from −80° C. and +20° C., preferably in the range from −20° C. and −10° C. A good effect can be observed even at a low fluorine concentration of up to 10% by volume.

Depending on the duration of the treatment or the amount of purifying agent used, the impurities can be, more or less, completely separated. For instance, if less fluorine is used than is required for attachment to the unsaturated impurities, a corresponding amount of impurities remains in the product to be purified. This can be determined, however, by simple manual experiments and product analysis. The treatment with elemental fluorine or a mixture of fluorine and inert gas is preferably continued for such a time until a 1,1,1,3,3-pentafluorobutane is obtained with a maximum content of 20 ppm of unsaturated chlorine-fluorine compounds and 10 ppm of unsaturated C2 compounds. The content of hydrogen chloride and/or hydrogen fluoride is run until a maximum of 1 ppm of each is contained. To this end, a treatment with amorphous silicon dioxide or aluminum oxide is used in particular.

If the crude product has been treated with a diatomic molecule, the separation of the resulting product into pure pentafluorobutane and other halogenated hydrocarbons can be effected by fractional condensation or, for example, also by distillation.

The process according to the invention makes it possible to produce 1,1,1,3,3-pentafluorobutane with a maximum concentration of 1 ppm of HF, 1 ppm of HCl, 10 ppm of unsaturated (chlorine) fluorine compounds and 10 ppm of unsaturated C2 compounds. Such highly pure pentafluorobutane is novel and is likewise a subject of the present invention.

The process according to the invention is outstandingly suitable for purifying 1,1,1,3,3-pentafluorobutane which is contaminated with fluorotricholoroethylene (as the only impurity or a component of impurities). It has been found that fluorotrichloroethylene is particularly difficult to separate since it is very unreactive. The process according to the invention makes it possible to decrease even this impurity to a maximum concentration of 20 ppm, and even to a concentration of less than 0.1 ppm.

Due to its low reactivity, fluorotrichloroethylene can be used as a control substance when monitoring the purification of 1,1,1,3,3-pentafluorobutane which is contaminated with fluorotrichloroethylene and further unsaturated compounds. Surprisingly it was found that only the decrease in the concentration of fluorotrichloroethylene needs to be monitored and the simultaneous monitoring of the decrease in the concentration of other unsaturated compounds may be dispensed with. Once fluorotrichloroethylene has been decreased to the desired level, other unsaturated compounds are likewise depleted. The use of fluorotrichloroethylene as a control substance when monitoring the purification of 1,1,1,3,3-pentafluorobutane, which contains fluorotrichloroethylene as well as further unsaturated compounds as impurities, is also a subject of the invention. Monitoring can be effected by means of GC-MS (SIM run=Selective Ion Mass). The detection limit for CFC1111 when determined by means of gas chromatography (GC)—thermal conductivity detection (t.c.d.)—is 100 ppm. With GC-MS in the SIM run mode (SIM run status), the detection limit is 0.1 ppm of CFC1111.

The purification process according to the invention makes it possible to produce highly pure 1,1,1,3,3-pentafluorobutane. Until now such purification operations were conducted only with highly stable fluorinated or fully halogenated compounds. Particularly the treatment with elemental fluorine produces a surprising result since, instead of the addition to the unsaturated compounds, a substitution reaction on the pentafluorobutane with formation of hexafluorobutane, heptafluorobutane or perfluorobutane would have been expected. The use according to the invention of fluorotrichloroethylene as a control substance in monitoring saves time, since it makes it possible in the recording or analysis of spectra to concentrate on the range in which fluorotrichloroethylene is registered. Working in the liquid phase saves energy.

The following examples are intended to explain the invention in further detail without limiting its scope. All experiments were carried out in the liquid phase.

EXAMPLE 1
Separation of Unsaturated Components
a) HFC365mfc with 0.22% (percent surface area in the gas chromatogram) CFC-1111 and 99.4% HFC365mfc was used.
aI) 84.8 g of the crude product was reacted with 6.8 g chlorine in the presence of 0.2 g $FeCl_3$ at 40° C. The reaction mixture was distilled. 0.11% CFC-1111 was detected in the distillate. Thus the amount of this impurity was decreased by half.
aII) 115.3 g of the crude product was hydrogenated in an autoclave with 0.8 g $H_2$ in the presence of a catalyst (4.5% by weight Pd, 0.5% by weight Rh on activated carbon). The reaction mixture contained only 0.03% CFC-1111.
b) HFC365mfc was used as the crude product with 0.16% (percent surface area in the gas chromatogram) CFC-1111 and 99.68% HFC365mfc.
bI) 93.6 g of the crude product was reacted with 2.3 g iodine (in the form of $KI/I_2$). The reaction mixture contained only 0.08% CFC-1111.
bII) 195.6 g of the crude product was reacted with 0.72 liters of a $F_2/N_2$ mixture (10% $F_2$) at −20° C. No CFC-1111 was detectable in the reaction mixture.

EXAMPLE 2
Separation of CFC-1111 and Acid Components 272 kg HFC365mfc with a CFC-1111 content of approximately 0.2% (percent surface area in the GB) was used. This corresponds to about 2,000 ppm. The reaction was carried out in a recirculating reactor. With cooling to −12° C., 150 liters per hour of a $F_2/N_2$ mixture (3% by volume $F_2$) was passed through the reactor. Duration: 12 hours. The reaction mixture was then heated, and HFC365mfc was distilled off. The content of acid components (particularly HCl and HF) the distillate was contacted with an adsorbent composed of $SiO_2$. The adsorbent used for this purpose was "AF400®." This is an aluminum-free, bead-form $SiO_2$-based adsorbent with a pore diameter of 400 Å (40 nm), supplier: Kali-Chemie/Engelhard, Nienburg.

After separation of the HFC365mfc from the adsorbent, the HCl content was below 1 ppm, and the HF content was also below 1 ppm.

(Note: to determine the CFC-1111 content in the product, the SIM-MS status of the GC-MS device was run. First a calibration curve was prepared to determine the ion current at 0.1 ppm and 10 ppm of CFC-1111 (by means of mixtures of corresponding concentrations of HFC365mfc and CFC-1111 specially prepared for this purpose). The observed ion currents and the associated concentrations of CFC-1111 were then correlated by means of this calibration curve.

What is claimed is:

1. A process for producing purified 1,1,1,3,3-pentafluorobutane with a decreased content of HCl, HF and unsaturated impurities from crude 1,1,1,3,3-pentafluorobutane, said process comprising treating the crude 1,1,1,3,3-pentafluorobutane in the liquid phase with a solid, inorganic sorption agent or with diatomic molecules selected from the group consisting of HCl, elemental fluorine and elemental chlorine which add to C—C-multiple bonds, and separating the treated 1,1,1,3,3-pentafluorobutane.

2. A process according to claim 1, wherein the crude 1,1,1,3,3-pentafluorobutane is treated with a solid, inorganic sorption agent selected from the group consisting of activated carbon and sorbents composed of aluminum oxide or silicon dioxide.

3. A process according to claim 2, wherein at least one acid selected from the group consisting of HCl and HF is separated from the crude 1,1,1,3,3-pentafluorobutane by the treatment with the sorption agent.

4. A process according to claim 1, wherein the treatment with the sorption agent is carried out at a temperature in the range from −30 to +100° C.

5. A process according to claim 4, wherein the treatment with the sorption agent is carried out at a temperature in the range from 15 to 25° C.

6. A process according to claim 1, wherein the crude 1,1,1,3,3-pentafluorobutane is treated with a diatomic molecule selected from the group consisting of HCl, elemental fluorine and elemental chlorine to decrease the unsaturated compound content of the 1,1,1,3,3-pentafluorobutane.

7. A process according to claim 6, wherein the crude 1,1,1,3,3-pentafluorobutane is treated with elemental fluorine in admixture with an inert gas.

8. A process according to claim 6, wherein the crude 1,1,1,3,3-pentafluorobutane is treated with elemental fluorine at a temperature in the range from −80 to +20° C.

9. A process according to claim 6, wherein the crude 1,1,1,3,3-pentafluorobutane is treated with elemental fluorine or with a mixture of fluorine and an inert gas until a purified 1,1,1,3,3-pentafluoro-butane product is obtained containing not more than 20 ppm unsaturated (chlorine)-fluorine compounds and not more than 10 ppm unsaturated C2-compounds.

10. A process according to claim 2, wherein the crude 1,1,1,3,3-pentafluorobutane is treated with amorphous $SiO_2$ or $Al_2O_3$ until a purified 1,1,1,3,3-pentafluoro-butane product is obtained containing not more than 1 ppm HCl and not more than 1 ppm HF.

11. 1,1,1,3,3-pentafluorobutane containing not more than 1 ppm HF, not more than 1 ppm HCl, not more than 20 ppm unsaturated (chlorine)-fluorine compounds, and not more than 10 ppm unsaturated C2 compounds.

12. A method of monitoring purification of an impure 1,1,1,3,3-pentafluorobutane containing unsaturated impurities including fluorotrichloroethylene, said method comprising measuring the fluorotrichloroethylene content of the 1,1,1,3,3-pentafluorobutane undergoing purification until a desired low level of fluorotrichloroethylene is detected.

* * * * *